United States Patent [19]
Koslo et al.

[11] Patent Number: 5,185,144
[45] Date of Patent: Feb. 9, 1993

[54] GASTROPROTECTANT COMPOSITIONS AND USE THEREOF

[75] Inventors: Randy Koslo, Cranbury; Alison Lukacsko, Robinsville, both of N.J.

[73] Assignee: Bristol-Myers Squibb Company, New York, N.Y.

[21] Appl. No.: 603,496

[22] Filed: Oct. 26, 1990

[51] Int. Cl.$^5$ .......................... A61K 7/34; A61K 7/38
[52] U.S. Cl. ......................................... 424/66; 424/68
[58] Field of Search ..................................... 424/66, 68

[56] References Cited
PUBLICATIONS

Chem. Abst(1), vol. 112-83877(W) (1990).
Chem. Abst(2), vol. 98-8194K (1983).
Merck Index, #342 9th Ed (1978).

*Primary Examiner*—S. J. Friedman
*Attorney, Agent, or Firm*—M. S. Simon

[57] ABSTRACT

Oral compositoins containing a gastroprotective amount of zirconium-aluminum glycinate, aluminum chlorohydrate or a mixture thereof are disclosed. A method for protecting the gastric mucosa against injury caused by a gastric irritant such as NSAIDs is also disclosed.

13 Claims, No Drawings

GASTROPROTECTANT COMPOSITIONS AND USE THEREOF

BACKGROUND OF INVENTION

The present invention relates to compositions containing a cytoprotective amount of "ZAG", "ACH" or a mixture thereof. Zirconium-aluminum glycinate aluminum chlorohydrate and mixtures thereof are preferred. Oral compositions of the invention are particularly useful as gastroprotectants in conditions where gastric prostaglandin synthesis is compromised. Consequently, the instant invention also relates to a method for protecting the gastric mucosa against injury caused by a gastric irritant such as an NSAID. Such method involves administration of a gastroprotectant of the invention.

DESCRIPTION OF THE PRIOR ART

Certain metal salts are known in the art as being cytoprotective. For example, aluminum hydroxide, aluminum sulfate, sucralfate and aluminum-magnesium antacid gel (see Hollander et al Scand. J. Gastroenterol 1986, 21 (Suppl 125) 151-153), acidified aluminum antacids (see Mir et al. U.S. Pat. No. 4,857,324), cadmium chloride, zinc chloride copper, iron, manganese (see Dupuy and Szabo, Gastroenterology, 91(4) 1986, 966-974) and bismuth (see Pugh et al., Br. J. Exp. Pathol, (UK) 1988, 69/6 (833-838)) have been reported to be effective in reducing ethanol-induced gastric lesions in the rat. It is known in the art that not all metallic salts have cytoprotective activity. For example, Mir et al. (cited above) report that aluminum chloride and acidified aluminum phosphate antacids were ineffective as cytoprotectants in the rat model. Domschke et al. (Scand. J. Gastroenterol 1986, 21 (Suppl 125) 144-149) report that calcium antacids were ineffective as cytoprotectants.

Thus it is clear that one skilled in the art can not predict whether a metal salt having unknown activity will function as a cytoprotectant.

Zirconium salts, in particular, zirconium.aluminium glycinate ("ZAG") and aluminum chlorohydrate ("ACH"), are water soluble basic aluminum hydrolysis complexss known in the art for their topical antiperspirant activity. Such compounds are acidic in nature and consequently would be considered by one skilled in the art to be devoid of antacid properties. Moreover, to our knowledge these metal salts have heretofore only been used topically. Surprisingly and unexpectedly, the present inventors have discovered that ZAG and ACH are gastroprotectants characterized by rapid onset and long duration of effect. ZAG and ACH gastroprotective efficacy is independent of endogenous prostaglandins. Consequently, ZAG and ACH are particularly useful as gastroprotectants in situations where gastric prostaglandin synthesis is compromised.

It should be appreciated that as used herein, "ZAG" and "ACH" include their respective activated species.

"ACH" generally encompasses aluminum salts having the empirical formula $Al_2(OH)_m(X)_n$ wherein $m+n=6$ and X represents cl, Br, I or $NO_3$. Compounds wherein X is Cl are preferred.

An especially preferred species is where X is Cl, m is 5 and n is 1. The resultant compound is generally known as aluminum chlorohydrate.

Another preferred species is where X is Cl, m is 4.5 and n is 1 5.

Yet another preferred species is where X is Cl, m is 4 and n is 2.

These salts are very complex systems in aqueous solution, containing varying compositions of polymeric, oligomeric, dimeric, and monomeric species.

"ZAG" generally encompasses basic aluminum/zirconium salts produced by reactions of aluminum chlorohydrate with various hydrolyzed basic zirconium chlorohydrates.

Basic aluminum/zirconium salts represent extremely complex antiperspirant salt systmesand are usually-prouced by reations of aluminum chlorohyrate with various hydrolyzedbasic zirconium chlorohydrates such as zirconium oxydichlorohydrate or zirconyl chloride, $ZrOCl_2$, and zirconium oxyhydroxychlorohydrate or zirconyl hydroxychloride, $ZrO(OH)Cl$, the FDA-OTC monograph (1982) identifies specific Al/Cl and Al/Zr mole ratios to designate or describe a specific salt system. For example, the ZAG salt of the composition $2Al_2(OH)_5Cl.ZrO(OH)Cl.glycine$ has a 4:1 Al/Zr ratio, a 4.3 or 1.5:1 Al/Cl ratio, and a 1.1 Zr/glycine ratio. This salt is referred to as an aluminum/zirconium tetrachlorohydrex (Al/Zr=2.0-6.0, and Al/Cl=1.5-0.9).

To illustrate the present invention the anti-lesion properties of ZAG and ACH were characterized using rat and hamster gastic lesion models. The methodology employed and results obtained are as set forth hereinbelow and in the Examples which follow.

The general methodology employed in the rat model with as follows:

Male Wistar-Kyoto rats (Taconic), weighing 175-225 g, were used.

Test animals were fasted overnight before experiments were carried out. The animals were allowed free access to water. Experiments were conducted as described below. Depending on the experiment, stomachs were removed 1, 2 or 4 hours after being dosed with damage-inducing agent (i.e. ethanol, indomethacin, HCl, acidified aspirin, seratonin). All stomachs were opened along the greater curvature and the stomach contents were gently washed away with $H_2O$. The stomachs were placed flat, mucosal side up, on filter paper moistened with physiological saline. Stomachs were photographed.

Stomach lesions were measured on each photo using a metric ruler. HCl, acidified aspirin, and indomethacin were found to produce thin lesions. The lesion score for each stomach was calculated as the accumulated lesion length per stomach and was divided by 2 to adjust for magnification in the photo. Ethanol was found to produce thick lesions that were scored as the lesion area ($mm^2$). The lesion score for ethanol-induced lesions was determined by measuring the total lesion area/stomach and dividing by 4 to adjust for magnification. The percent inhibition of lesion formation (I) was calculated as:

$$I = \left( \frac{\text{lesion score (controls)} - \text{lesion score (treated)}}{\text{lesion score (controls)}} \right) \times 100$$

The general methodology employed in the hamster model was as follows:

Mabe Golden Syrian Hamsters (Harlan Sprague Dawleym, Inc.), weighing 99-146 g, were used.

Test animals were fastened for 24 hours before experiments were carried out. The animals were allowed free access to water. 2½ hours after aspirin administration (500 mg/kg), stomachs were removed and opened along the greater curvature. Stomach contents were gently washed away with H₂O. The stomachs were placed flat, mucosal side up, on filter paper moistened with physiological saline. Stomachs were photographed.

Stomach lesions were measured on each photo using a metric ruler. Aspirin was found to produce thin lesions. The lesion score for each stomach was calculated as the accumulated lesion length per stomach divided by 2 to adjust for magnification in the photo. The percent inhibition of lesion formation (I) was calculated as:

$$I = \left( \frac{\text{lesion score (controls)} - \text{lesion score (treated)}}{\text{lesion score (controls)}} \right) \times 100$$

It should be noted that in the Tables of the Examples which follow, all data are expressed as % protection, as compared to water pretrsatment groups.

EXAMPLES 1-5

Utilizing the rat model methodology detailed heretofore, specific damaging agents were evaluated.

1. Ethanol-Induced Lesions

The aluminum compounds (10–600mg/kg) were dosed p.o. one hour prior to ethanol 100% (3ml/kg) p.o. The test animals were sacrificed one hour later and the stomachs scored. The results are set forth in the following Table 1.

TABLE 1

| Agent | mg/kg | Time of Administration | % Protection |
|---|---|---|---|
| ZAG | 10 p.o. | 60 min. prior to administration of ethanol | 58.1 ± 13.9 |
| ZAG | 100 p.o. | 60 min. prior to administration of ethanol | 92.0 ± 3.2 |
| ZAG | 600 p.o. | 60 min. prior to administration of ethanol | 99.8 ± 0.14 |
| ACH | 10 p.o. | 60 min. prior to administration of ethanol | 27.1 ± 21.1 |
| ACH | 100 p.o. | 60 min. prior to administration of ethanol | 92.1 ± 3.6 |
| ACH | 600 p.o. | 60 min. prior to administration of ethanol | 77.2 ± 9.12 |

2. Indomethacin-Induced Lesions

The aluminum compounds (600m8/k8) were dosed p.o. one hour prior to indomethacin (30m8/kg, 3 ml/kg) p.o. The test animals were sacrificed four hours later and the stomachs scored. The results are set forth in the following Table 2.

TABLE 2

| Agent | mg/kg | Time of Administration | % Protection |
|---|---|---|---|
| ZAG | 600 p.o. | 60 min. prior to administration of indomethacin 30 mg/kg 3 ml/kg | 99.51 ± 0.25 |
| ACH | 600 p.o. | 60 min. prior to administration of indomethacin 30 mg/kg 3 ml/kg | 98.58 ± 0.72 |

3. Hydrochloric Acid-Induced Lesions

The aluminum compounds (600 mg/kg) were dosed p.o. one hour prior to 0.75 N hydrochloric acid (3 ml/kg) p.o. The test animals were sacrificed one hour late and the stomachs scored. The results are set forth in the following Table 3.

TABLE 3

| Agent | mg/kg | Time of Administration | % Protection |
|---|---|---|---|
| ZAG | 600 p.o. | 60 min. prior to administration of 0.75 N HCl 3 ml/kg | 66.80 ± 10.10 |
| ACH | 600 p.o. | 60 min. prior to administration of 0.75 N HCl 3 ml/kg | 93.48 ± 1.02 |

4. Acidified Aspirin-Induced Lesions

The aluminum compounds (600 mg/kg) 6 ml/kg were dosed p.o. one hour prior to acidified aspirin [80 mg/kg (150 mM HCl), 6 ml/kg] p.o. The test animals were sacrificed two hours later and the stomachs scored. The results are set forth in the following Table 4.

TABLE 4

| Agent | mg/kg | Time of Administration | % Protection |
|---|---|---|---|
| ZAG | 600 p.o. | 60 min. prior to administration of acidified aspirin 80 mg/kg 6 ml/kg | 84.97 ± 3.22 |
| ACH | 600 p.o. | 60 min. prior to administration of acidified aspirin 80 mg/kg 6 ml/kg | 80.75 ± 9.97 |

5. Serotonin-Induced Lesions

The aluminum compounds (600 mg/kg) were dosed p.o. one hour prior to serotonin (60 ml/kg, 2 ml/kg s.c.). The test animals were sacrificed four hours late ad the stomachs scored. The results are set forth in the following Table 5.

TABLE 5

| Agent | mg/kg | Time of Administration | % Protection |
|---|---|---|---|
| ZAG | 600 p.o. | 60 min. prior to administration of 60 mg serotonin 2 ml/kg | −64.60 ± 29.67 |
| ACH | 600 p.o. | 60 min. prior to administration of 60 mg serotonin 2 ml/kg | 36.77 ± 9.27 |

EXAMPLES 6-7

Utilizing the rat methodology detailed heretofore, thiol depletion was evaluated.

6. Ethanol-Induced Lesions n-ethylmaleimide (5 mg/kg, 2 ml/kg i.p.) was administered one hour prior to dosage of the test aluminum compound (600 mg/kg). One hour after administration of the aluminum compound, the animals received ethanol 100% (3 ml/kg p.o.). Test animals were sacrificed one hour later and the stomachs were scored. The results are set forth in the following Table 6.

TABLE 6

| Agent | mg/kg | Time of Administration | % Protection |
|---|---|---|---|
| ZAG with n-ethyl-maleimide pretreatment | 600 p.o. 5 i.p. | 60 min. prior to administration of ethanol 120 min. prior to administration of ethanol | 8.3 ± 32.5 |
| ZAG without n-ethyl-maleimide pretreatment | 600 p.o. | 60 min. prior to administration of ethanol | 98.9 ± 0.5 |
| ACH with n-ethyl-maleimide pretreatment | 600 p.o. 5 i.p. | 60 min. prior to administration of ethanol 120 min. prior to administration of ethanol | −5.5 ± 22.0 |
| ACH without n-ethyl-maleimide pretreatment | 600 p.o. | 60 min. prior to administration of ethanol | 97.8 ± 2.0 |

7. Acidified Aspirin-Induced Lesions

The procedure was similar to that employed for ethanol-induced lesions in Example 6 above, however, one hour after administration of the aluminum compound, the animals received acidified aspirin [80 mg/kg (150 mM HCl) 6 ml/kg] p.o. instead of ethanol. The animals were sacrificed two hours lateral and stomachs were scored. The results are set forth in the following Table 7.

TABLE 7

| Agent | mg/kg | Time of Administration | % Protection |
|---|---|---|---|
| ZAG with n-ethyl-maleimide pretreatment | 600 p.o. 2 ml/kg i.p. | 60 min. prior to administration of acidified aspirin 120 min. prior to administration of acidified aspirin | 93.15 ± 4.24 |
| ACH with n-ethyl-maleimide pretreatment | 600 p.o. 2 ml/kg i.p. | 60 min. prior to administration of acidified aspirin 120 min. prior to administration of acidified aspirin | 95.78 ± 1.29 |

EXAMPLES 8–9

Utilizing the rat model methodology detailed heretofore, endogenous prostaglandin depletion was evaluated.

8. Ethanol-Induced Lesions

Indomethacin (20 mg/kg, 2 ml/kg p.o.) was administered one hour prior to dosage of the test aluminum compound. One hour after dosage of the aluminum compound, the animals received ethanol 100% (3 ml/kg p.o.) The animals were scarified one hour later and the stomachs were scored. The results are as set forth in the following Table 8.

TABLE 8

| Agent | mg/kg | Time of Administration | % Protection |
|---|---|---|---|
| ZAG with indomethacin pretreatment | 600 p.o. 20 p.o. | 60 min. prior to administration of ethanol 120 min. prior to administration of ethanol | 91.4 ± 3.2 |
| ZAG without indomethacin pretreatment | 600 p.o. | 60 min. prior to administration of ethanol | 81.2 ± 5.4 |
| ACH with indomethacin pretreatment | 600 p.o. 20 p.o. | 60 min. prior to administration of ethanol 120 min. prior to administration of ethanol | 83.3 ± 9.3 |
| ACH without indomethacin pretreatment | 600 p.o. | 60 min. prior to administration of ethanol | 90.9 ± 3.3 |

9. Acidified Aspirin-Induced Lesions

The procedure was the same as that employed for ethanol-induced lesions in Example 6 above, however, one hour after the administration of the aluminum compound, the animals receive acidified aspirin [80 mg/kg (150 mM HCl) 6 ml/kg] p.o. rather than ethanol the animals were sacrificed two hours later and the stomachs were scored. The results are set forth in the following Table 9.

TABLE 9

| Agent | mg/kg | Time of Administration | % Protection |
|---|---|---|---|
| ZAG | 600 p.o. (6 ml/kg) | 60 min. prior to acidified aspirin | 93.51 ± 2.61 |
| Indomethacin | 20 p.o. (2 ml/kg) | 120 min. prior to acidified aspirin | |
| ACH | 600 p.o. (6 ml/kg) | 60 min. prior to acidified aspirin | 98.78 ± 0.72 |
| Indomethacin | 20 p.o. (2 ml/kg) | 120 min. prior to acidified aspirin | |

EXAMPLES 10–11

Utilizing the rat model methodology detailed heretofore, onset/duration was evaluated.

10. Ethanol-Induced Lesion

The aluminum compounds (600 mg/kg) were administered 5, 30, 60 or 180 minutes before administration of ethanol (100%, 3 ml/kg p.o.). The animals were sacrified one hour after ethanol administration and the stomach were scored. The results are set forth in the following Table 10.

TABLE 10

| Agent | mg/kg | Time of Administration | % Protection |
|---|---|---|---|
| ZAG | 600 p.o. | 5 min. prior to ethanol | 70.7 ± 7.4 |
| ZAG | 600 p.o. | 30 min. prior to ethanol | 83.4 ± 5.5 |
| ZAG | 600 p.o. | 60 min. prior to ethanol | 70.6 ± 5.8 |
| ZAG | 600 p.o. | 180 min. prior to ethanol | 97.4 ± 1.0 |
| ACH | 600 p.o. | 5 min. prior to ethanol | 92.4 ± 3.0 |
| ACH | 600 p.o. | 30 min. prior to ethanol | 97.5 ± 0.8 |
| ACH | 600 p.o. | 60 min. prior to ethanol | 89.5 ± 7.1 |
| ACH | 600 p.o. | 180 min. prior to ethanol | 98.1 ± 0.7 |

11. Acidified Aspirin-Induced Lesions

The aluminum compounds (600 mg/kg) were administered 5, 30, 60 or 180 minutes before administration of the acidified aspirin [80 mg/kg (150 mM HCl), 6 ml/kg] p.o. Test animals were sacrificed two hours after acidified aspirin administration and the stomachs were scored. The results are set forth in following Table 11.

TABLE 11

| Agent | mg/kg | Time of Administration | % Protection |
|---|---|---|---|
| ZAG | 600 p.o. | 5 min. prior to acidified aspirin | 10.97 ± 42.24 |
| ZAG | 600 p.o. | 30 min. prior to acidified aspirin | 61.84 ± 17.70 |
| ZAG | 600 p.o. | 60 min. prior to acidified aspirin | 87.28 ± 2.82 |
| ZAG | 600 p.o. | 180 min. prior to acidified aspirin | 91.48 ± 2.24 |
| ACH | 600 p.o. | 5 min. prior to acidified aspirin | 77.00 ± 7.27 |
| ACH | 600 p.o. | 30 min. prior to acidified aspirin | 89.13 ± 7.52 |
| ACH | 600 p.o. | 60 min. prior to acidified aspirin | 93.70 ± 2.44 |
| ACH | 600 p.o. | 180 min. prior to acidified aspirin | 97.92 ± 0.95 |

EXAMPLE 12

Utilizing the hamster model methodology detailed heretofore, aspirin induced lesions were evaluated.

12. Aspirin-Induced Lesions

The aluminum compounds (600 mg/kg) were dosed p.o. one hour prior to aspirin (500 mg/kg, 10 ml/kg) p.o. 2½ hours after aspirin administration the animals were sacrificed. The stomachs were removed, rinsed, photographed and scored. The results are set forth in the following Table 12.

TABLE 12

| Agent | mg/kg | Time of Administration | % Protection |
|---|---|---|---|
| ZAG | 600 p.o. | 60 min. prior to aspirin | 85.17 ± 5.18 |
| ACH | 600 p.o. | 60 min. prior to aspirin | 82.35 ± 4.13 |

As is evident from the data of Table 10, the % protection was over 70%. Moreover, it reached statistical significance for the metal salt treatments regardless of the time of pretreatment.

As is evident from the data of Tables 1-12, ACH and ZAG provide gastroprotection against a variety of mucosal damaging agents. The protective efficacy against ethanol and NSAID-induced damage demonstrates the utility of AGH and ZAG in protecting the stomach in situations of over indulgence and therapy with analgesics/antiinflammatory drugs, respectively. Since the data demonstrates that AcH and ZAG also protected against damage caused by an exogenous source of the same acid secreted by the stomach (HCl), ACH and ZAG would be effective in the prevention and treatment of ulcer disease.

Serotonin is a damaging agent used to determine if the gastroprotective mechanism of action of a compound is via effects on the vasculature. Lack of efficacy by ZAG against serotonin (as shown in Table 5) merely indicates that ZAG probably does not impart protection against the other damaging agents by an effect on the vasculature.

The data of Tables 1-12 indicate that ZAG and ACH do not appear to be dependent on endogenous prostaglandins for their gastroprotective effects. These compounds would therefore, be expected to be very effective in preventing damage in potential states of prostaglandin depletion such as during NSAID therapy.

Endogenous thiols are required for ZAG and ACH to protect against gastric damage caused by ethanol but not aspirin. This is reflective of the different mechanism by which ethanol and aspirin cause damage and serves to demonstrate that ZAG and ACH are effective gastro protectants regardless of the mechanism by which the mucosal damaging agents work.

As is evidenced by the data of Tables 10 and 11, ZAG and ACH have a rapid onset of effect. Their duration of activity is also substantial.

As is evidenced by the data of Table 12, protection was afforded by ZAG and AcH in the hamster model. This demonstrates that ZAG and ACH are effective across species.

The present invention also encompasses compositions for protecting the gastric mucosa against injury caused by gastric irritants such as NSAIDs. Such compositions comprise a gastroprotective amount of a gastroprotectant selected from the group consisting of ZAG, AGH and mixtures thereof, and a pharmaceutically acceptable carrier, said composition being in oral unit dosage form.

When the gastroprotectant is ZAG, it is generally present in an amount of from about 100 mg to about 2 gm, per unit dose of composition. Preferably, ZAG is present in an amount of about 400 mg to about 1000 mg, per unit dose of composition. More preferably, it is present in an amount of about 600 mg, per unit dose of composition.

When the gastroprotectant is AcH, it is generally present in an amount of from about 100 m8 to about 2 gm, per unit dose of composition. Preferably, ACH is present in an amount of about 400 mg to about 1000 mg, per unit dose of composition. More preferably, it is present in an amount of about 600 mg, per unit dose of composition.

When a mixture of ZAG and ACH is employed as the gastro. protectant, the ZAG and ACH are respectfully present in each unit dose of composition such that the total amount of gastroprotectant is from 100 mg-2 gm per unit dose.

The preparation of compositions of the present is facilitated by the water solubility of the gastroprotectants of the invention.

Oral compositions of the present invention may take the form of solutions, tablets, capsules, bulk powders, etc. Such dosage forms may be prepared by methods well known in the art.

What is claimed is:

1. A method for protecting the gastric mucosa against injury caused by a gastric irritant, comprising administering with or before administration of the gastric irritant, a gastro protective amount of a gastroprotectant selected from the group consisting of ZAG, ACH and a mixture thereof.

2. The method, as claimed in claim 1, wherein the gastroprotectant is ZAG.

3. The method, as claimed in claim 1, wherein the gastroprotectant is ACH.

4. The method, as claimed in claim 1, wherein the gastroprotectant is a mixture of ZAG and ACH.

5. The method, as claimed in claim 2, wherein the ZAG is present in an amount of about 100 mg to about 2 gm, per unit dose of the composition.

6. The method as claimed in claim 2, wherein the ZAG is present in an amount of about 400 mg to about 1000 mg, per unit dose of the composition.

7. The method, as claimed in claim 2, wherein 600 mg ZAG is present in each unit dose of the composition.

8. The method, as in claim 3 wherein the ACH is present in an amount of about 100 mg to about 2 gm, per unit dose of the composition.

9. The method, as claimed in claim 3, wherein the ACH is present in an amount of about 400 mg to about 1000 mg, per unit dose of the composition.

10. The method, as claimed in claim 3, wherein 600 mg ACH is present in each unit dose of the composition.

11. The method, as claimed in claim 4, wherein each unit dose of the composition contains the mixture of ZAG and ACH in a total amount of about 100 mg to about 2 gm.

12. The method, as claimed in claim 11 wherein said total amount is from about 400 mg to about 1000 mg.

13. The method, as claimed in claim 11, wherein said total amount is 600 mg.

* * * * *